United States Patent [19]

Gamble et al.

[11] Patent Number: 5,672,780

[45] Date of Patent: Sep. 30, 1997

[54] PURIFICATION OF ETHYLENE GLYCOL RECOVERED FROM POLYESTER RESINS

[75] Inventors: William James Gamble, Rochester; Andrius Algimantas Naujokas, Webster, both of N.Y.

[73] Assignee: Eastman Kodak Company, Rochester, N.Y.

[21] Appl. No.: 687,822

[22] Filed: Jul. 26, 1996

[51] Int. Cl.⁶ .................................................. C07C 27/26
[52] U.S. Cl. ...................................... 568/871; 568/858
[58] Field of Search ................................. 568/871, 858

[56] References Cited

U.S. PATENT DOCUMENTS

| | | | |
|---|---|---|---|
| 3,367,847 | 2/1968 | Pierson | 203/41 |
| 3,491,161 | 1/1970 | Pitts | 260/637 |
| 4,028,195 | 6/1977 | Becker et al. | 203/38 |
| 4,519,875 | 5/1985 | Becker et al. | 203/28 |
| 4,830,712 | 5/1989 | Crandall et al. | 203/35 |
| 5,051,528 | 9/1991 | Naujokas et al. | 560/78 |
| 5,298,530 | 3/1994 | Gamble et al. | 521/48.5 |
| 5,391,263 | 2/1995 | Hepner et al. | 203/51 |
| 5,432,203 | 7/1995 | DeBruin et al. | 521/48.5 |
| 5,578,173 | 11/1996 | Tott, Jr. et al. | 203/6 |

*Primary Examiner*—Samuel Barts
*Attorney, Agent, or Firm*—Joshua G. Levitt

[57] ABSTRACT

There is described a process for removing dimethyl terephthalate contaminants from ethylene glycol. The process comprises distilling ethylene glycol in the presence of an ester exchange catalyst to cause reaction between ethylene glycol and dimethyl terephthalate to form compounds that are less volatile than either ethylene glycol or dimethyl terephthalate, such as bishydroxyethyl terephthalate.

7 Claims, 2 Drawing Sheets

PURIFICATION OF ETHYLENE GLYCOL RECOVERED FROM POLYESTER RESINS

CROSS REFERENCE TO RELATED APPLICATION

Reference is made to and priority claimed from U.S. Provisional Application Serial No. US 60/002,179, filed 11 Aug. 1995, entitled PURIFICATION OF ETHYLENE GLYCOL RECOVERED FROM POLYESTER RESINS.

FIELD OF INVENTION

This invention relates to purification of ethylene glycol. In a particular aspect, it relates to purification of ethylene glycol that has been recovered from condensation-type polyester resins such as polyethylene terephthalate by low pressure methanolysis.

BACKGROUND OF THE INVENTION

Polyester resins have found widespread use in varied applications. Polyester resins, such as polyethylene terephthalate, are used in films, including photographic film, in fibers, and in food and beverage containers. Various methods have been disclosed for the depolymerization of such resins into their component monomers, such as ethylene glycol and terephthalic acid, or derivatives thereof, so that they could be reused.

Naujokas et al. U.S. Pat. No. 5,051,528 describes a low pressure methanolysis process of recovering ethylene glycol and dimethyl terephthalate from polyethylene terephthalate scrap resins by dissolving the polyester resin in oligomers of the same monomers as present in the polyester, passing super-heated methanol through the solution and recovering ethylene glycol and dimethyl terephthalate.

Gamble et al. U.S. Pat. No. 5,298,530, issued Mar. 29, 1994 describes improvements in this process. In this improvement the scrap resin is combined with reactor melt in a dissolver before the dissolver melt is transferred to the reactor for contact with super-heated methanol. In the reactor, polymers and oligomers are further depolymerized into component glycol and ester monomers, which are then are separated from higher boiling components with a rectifier and then recovered.

Further improvements and variations in this process are described in Gamble et al. U.S. Pat. No. 5,393,916 issued Feb. 28, 1995, and in Toot et al. U.S. Pat. No. 5,414,022 issued May 9, 1995.

The processes described in these patents reverse the polymerization reaction by which the polyethylene terephthalate is formed by depolymerizing polyethylene terephthalate to dimethyl terephthalate and ethylene glycol. They differ from prior processes in that the presence of the dissolver and the rectifier allows the process to be run at a lower pressure than prior art processes. The use of a rectifier, however, complicates the recovery of one of the components.

A typical process for the separation and recovery of dimethyl terephthalate and ethylene glycol exiting the rectifier is to remove excess methanol in a spray tower, crystallize dimethyl terephthalate, distill methanol and distill ethylene glycol. The remaining dregs, which contain higher glycols and oligomer, are discarded.

Although the recovery process is designed so that dimethyl terephthalate is removed first, some dimethyl terephthalate remains with the ethylene glycol and complicates its recovery by fouling the distillation column in which ethylene glycol is recovered. Thus, it would be desirable to provide a process for removing the dimethyl terephthalate from the ethylene glycol.

We have found that when ethylene glycol obtained in previously used high pressure recovery apparatus, which did not employ a rectifier, was distilled there was no fouling. We have determined that this was due to the presence of an ester exchange catalyst that was carried over with the material recovered. However, the existence of a rectifier in the low pressure apparatus prevents the catalyst from going to the recovery apparatus. Thus, the ethylene glycol that exits the rectifier in the low pressure methanolysis process is catalyst-free.

We have found that the problem can be solved by introducing an ester exchange catalyst so that distillation of the ethylene glycol occurs in its presence, thereby causing dimethyl terephthalate present to react with ethylene glycol to form bishydroxyethyl terephthalate. Since bishydroxyethyl terephthalate is less volatile than dimethyl terephthalate, it does not foul the distillation column to any appreciable extent, but is removed with the high boiling dregs.

The purification of ethylene glycol from various sources is described in U.S. Pat. Nos. 3,367,847, 3,491,161, 4,028,195, 4,519,875, 4,830,712, and 5,391,263. In particular, U.S. Pat. Nos. 3,491,161 and 5,391,263 indicate that ethylene glycol and dimethyl terephthalate remaining from the reactants for polyester synthesis form an azotrope which complicates the recovery of ethylene glycol. However, the sources of the ethylene glycol and the solutions employed in these patents are different from those of the present invention.

SUMMARY OF THE INVENTION

The present invention provides a process for removing dimethyl terephthalate contaminants from ethylene glycol recovered from scrap polyester by low pressure methanolysis, the process comprising a) adding an ester exchange catalyst to an otherwise catalyst-free mixture of dimethyl terephthalate and ethylene glycol and b) heating the mixture to convert dimethyl terephthalate to bishydroxyethyl terephthalate.

Typically heating is performed during the distillation step in which ethylene glycol is separated from the other components.

Thus, the present invention provides a simple, economic means for purifying ethylene glycol recovered from scrap polyester.

DETAILED DESCRIPTION OF THE INVENTION

Figure 1:
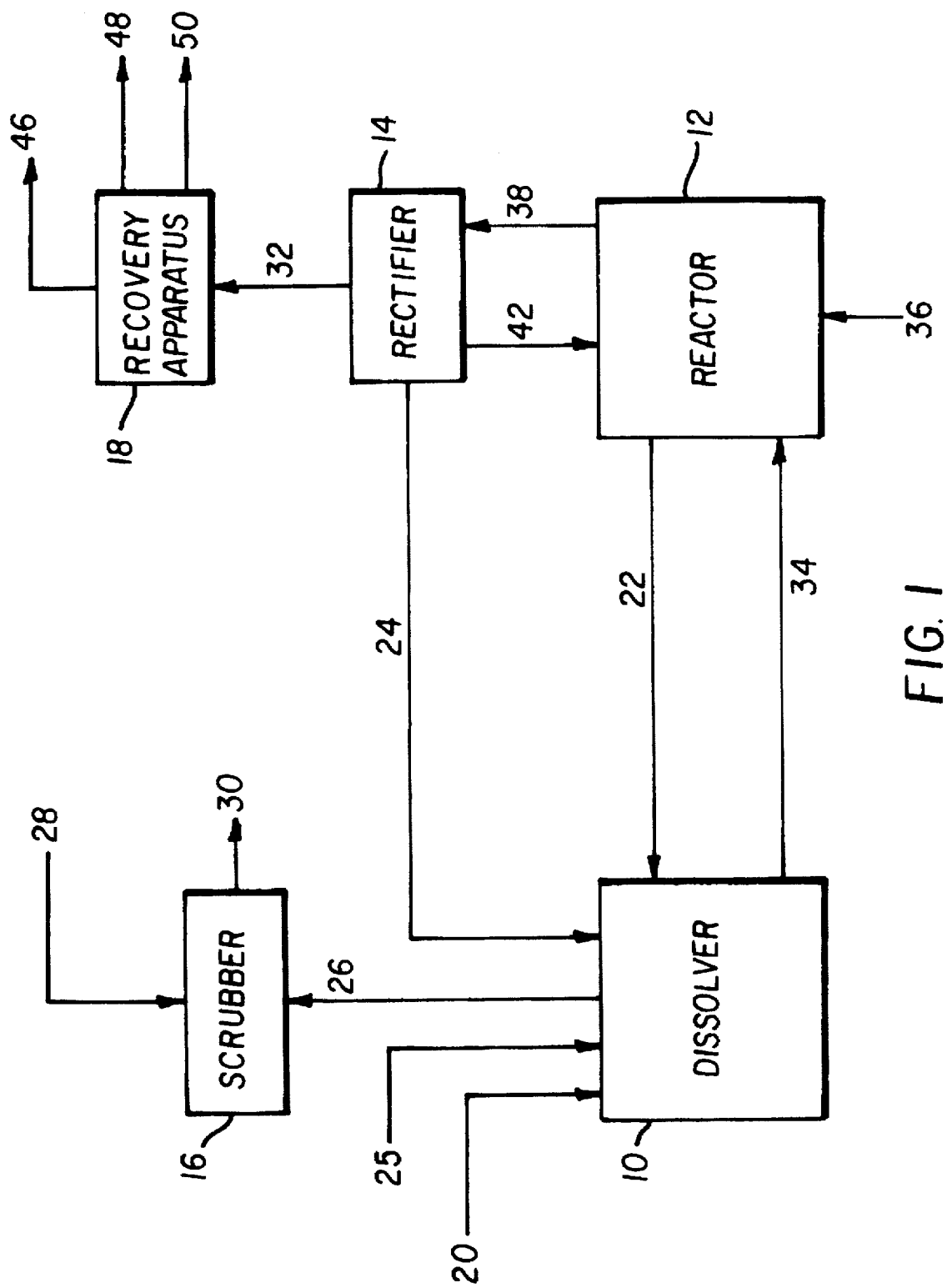
FIG. 1 is a schematic flow diagram illustrating preferred apparatus for low pressure methanolysis of polyester resins.

The present invention preferably is applied to ethylene glycol obtained from the apparatus and process depicted in FIG. 1. It can utilize apparatus shown in FIG. 2, which is an elaboration of the recovery apparatus (18) shown in FIG. 1.

The apparatus of FIG. 1. comprises:

a dissolver for receiving polyester, a reactor for depolymerizing polyester into monomer components, and a rectifier for separating monomer components.

This apparatus is used in a process which comprises the steps of:

a) adding polyester to the dissolver and combining it with melt from the reactor to reduce the chain length of the polyester, b) transferring reduced chain length polyester from the dissolver to the reactor, c) passing super-heated methanol through the reactor to depolymerize polyester into its constituent monomers, d) transferring depolymerization products from the reactor to the rectifier, e) separating the depolymerization products in the rectifier into a vapor phase containing monomer components and a liquid phase containing higher molecular weight materials, f) recovering and purifying ethylene glycol exiting the rectifier by i) adding an ester exchange catalyst to the ethylene glycol containing mixture and ii) heating the mixture to convert dimethyl terephthalate to bishydroxyethyl terephthalate.

The process and apparatus of FIG. 1 are described in detail in the Naujokas et al, Gamble et al. and Toot et al. patents referred to above, and their disclosures are incorporated herein by reference. In the apparatus of FIG. 1 a dissolver (10), a reactor (12), and a rectifier (14), are connected by the pipes, pumps and valves needed to transfer the reactants from one location to another in accordance with the reaction. Optionally included in this apparatus is a scrubber (16), for recovering gases from the dissolver.

In practice, polyethylene terephthalate (20) in a suitable form and size is introduced into the dissolver by any suitable means where it is liquefied and reduced in chain length. The dissolver can be run at atmospheric pressure. Thus, simple solids handling devices such as rotary air locks can be employed to introduce the polyester resin. Suitable means for introducing the polyester include an air conveyor, a screw feeder, an extruder, and the like.

The dissolver is equipped with means for heating its contents to a temperature of up to about 305° C. In practice the dissolver is maintained at a temperature in the range of 240° to 260° C.

One or both of the reactor melt (22) and the rectifier liquid (24) can be introduced into the dissolver via suitable piping. Reactor melt and rectifier liquid introduced into the dissolver react with the polyester to shorten the average chain length. This initiates the depolymerization reaction and decreases the viscosity of the dissolver contents. In addition, there can be added to the dissolver an ester exchange catalyst (25), such as zinc acetate. Such catalysts are known in the art to facilitate the depolymerization process.

The reactor melt and dissolver melt comprise methanol, low molecular weight polyesters, monomers, monohydric alcohol-ended oligomers, glycols, dimethyl terephthalate and methylhydroxyethyl terephthalate. The major difference between these two melts is the average chain length of the polyester. The rectifier liquid contains the same components except for polyesters.

The viscosity of the dissolver melt preferably is maintained in the range of 0.002 to 0.1 Pa.s. This is sufficiently low to permit the use of inexpensive pumping and heating means, and permits the reactor to be operated at optimum pressures to provide good yields of monomer. The flow rates of material in and out of the dissolver can be adjusted to maintain the viscosity at the desired level.

The gases (26) which evolve in the dissolver contain monomers that preferably are recovered together with the monomers exiting the reactor. This can be accomplished by passing the gases to the scrubber where they are treated with and absorbed by liquid methanol (28). This material (30) is then passed to the recovery apparatus (18) where it is combined with the vapor stream (32) exiting the rectifier for recovery.

Melt (34) from the dissolver is transferred to the reactor by suitable piping and pumps. Super-heated methanol vapor (36) is provided to the reactor by conventional means. The methanol introduced into the reactor heats the reactor contents and acts as a depolymerization agent. The effectiveness of the super-heated methanol for heating the reactor contents and for stripping reaction product depends on its volumetric flow rate; the depolymerization rate in the reactor therefore is a function of the methanol flow rate to the reactor. Methanol is introduced into the reactor at a rate in the range of 2 to 6 parts by weight methanol per part polyester.

There is transferred from the reactor to the rectifier a vapor stream (38) comprising methanol, dimethyl terephthalate, glycols including ethylene glycol, diethylene glycol, and triethylene glycol, dimethyl isophthalate, cyclohexanedimethanol, and methylhydroxyethyl terephthalate. The rectifier separates the higher boiling components, such as methylhydroxyethyl terephthalate and esterification catalyst from the vapor stream exiting the reactor. They can be routed to the dissolver in the form of a liquid (24) together with dimethyl terephthalate, glycols and methanol or all or portion can be returned to the reactor as a liquid (42).

The remainder of the vapor stream (32) is transferred from the rectifier to recovery apparatus (18), where methanol (46) is recovered for further use, and the glycol components (48) separated from the terephthalate components (50). This is illustrated in more detail in FIG. 2.

Figure 2:
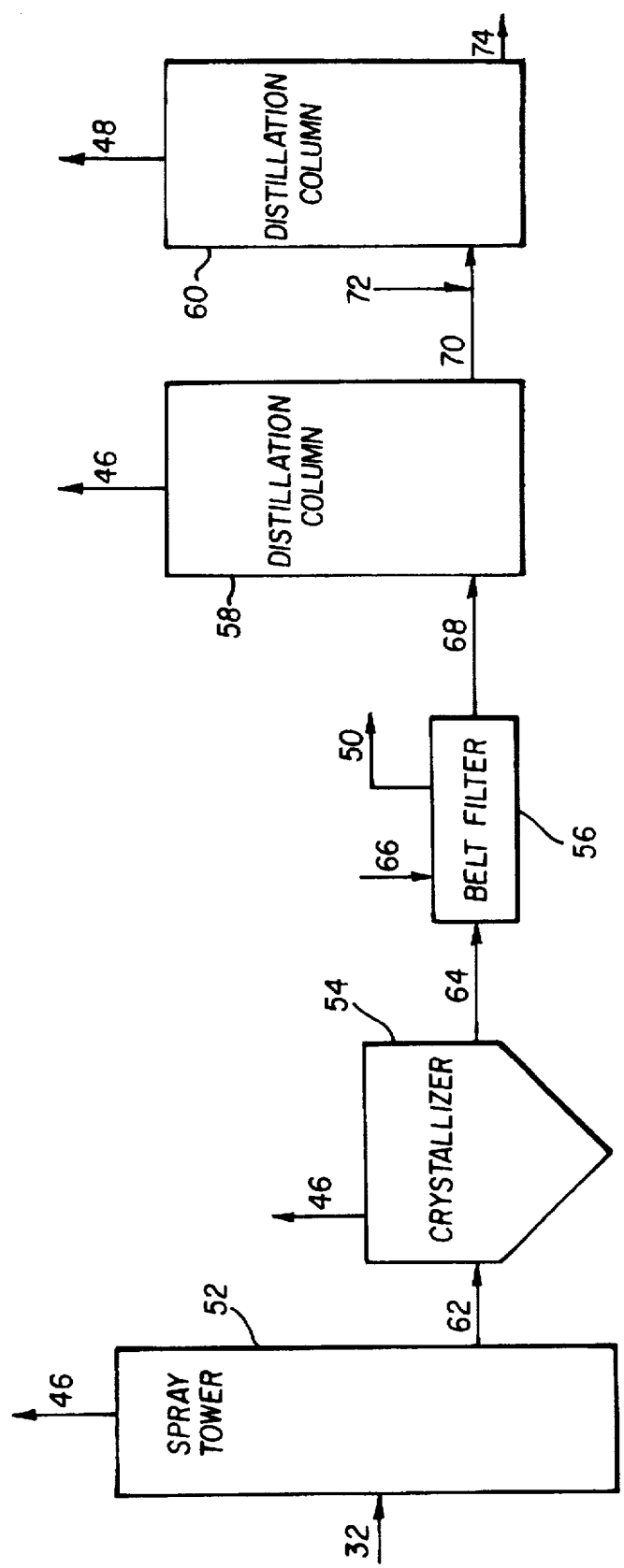
FIG. 2 is a schematic flow diagram illustrating preferred apparatus for the separation of the components recovered in accordance with FIG. 1.

As shown in FIG. 2, the output of the rectifier, which principally comprises methanol, dimethyl terephthalate and ethlyene glycol is sent to a spray tower (52), where the bulk of the methanol is removed. The spray tower is essentially a distillation column operated at a temperature in the range of 65° to 100° C. to condense the vapor stream exiting the rectifier. Methanol vapor is partially removed at the top of the column and the conditions of concentration and pressure are adjusted to maintained dimethyl terephthalate in solution. The solution (62) can be recirculated from the bottom of the tower to a higher level and sprayed on incoming vapor to facilitate cooling.

The solution (62), which comprises glycol and terephthalate components in residual methanol, is transferred to a crystallizer (54) and then to a belt filter to recover dimethyl terephthalate (50). In the crystallizer the dimethyl terephthalate is concentrated, additional methanol is recovered and the dimethyl terephthalate is precipitated. The crystallizer is operated at a temperature in the range of 25° to 65° C. and at atmospheric pressure. In the belt filter the dimethyl terephthalate crystals are purified by washing with liquid methanol (66) at a temperature in the range of 20° to 40° C. The dimethyl terephthalate product (50) can then be sent to further recovery operations consistent with the use to which it will be put.

The effluent (68) of the belt filter contains methanol, ethylene glycol and residual dimethyl terephthalate, and might contain higher glycols, other terephthalates and oligomers. Methanol is separated from the other components in a first distillation operation. This can be accomplished in a distillation column (58) operated at the temperature of the boiling point of methanol (65° C. at atmospheric pressure.).

While the preceding procedure represents a preferred way of recovering ethylene glycol, it will be appreciated that there are other ways of obtaining ethylene glycol that is contains residual dimethyl terephthalate. The remainder of the discussion is applicable to ethylene glycol obtained by the procedure just described, or by other procedures.

The higher boiling components (70) exiting the first distillation column are transferred to a second distillation column (60) operated at a temperature in the range of 100° to 230° C. and a pressure in the range of 3 to 30 psia. Because dimethyl terephthalate has a relatively high melting point (140° C.) and a narrow liquid phase range, it has a propensity to sublime and form a solid deposit. Also, dimethyl terephthalate and ethylene glycol form an azeotrope which prevents their complete separation from one another. Thus, unless it is converted to a compound with different characteristics, it will foul the distillation column (60) and require more frequent shut down for cleaning than otherwise would be necessary. The addition of an ester exchange catalyst (72), such as zinc acetate, facilitates reaction between dimethyl terephthalate and ethylene glycol to form methylhydroxyethyl terephthalate, which has a higher boiling point and, hence, less of a propensity to foul the distillation column. The catalyst can be introduced anywhere in the ethylene glycol mixture downstream of the rectifier. A convenient location is to introduce the catalyst (72) into the stream (70) going from the first distillation column to the second distillation column, or into the second distillation column.

In addition to zinc acetate, suitable catalysts include the conventional ester exchange and polycondensation catalysts, such as organic salts of zinc, titanium, germanium and the like. The catalyst can be introduced into the feed stream (70) in an amount of about 25 to 1000 parts by weight per million parts of the feed stream. Preferable about 100 to 250 parts per million catalyst are used.

The output of the second distillation column is ethylene glycol (48) and a waste stream (74) which is discarded or sent for further recovery, as appropriate.

EXAMPLE

The following example illustrate the invention.

To a 16 tray distillation column (shown in FIG. 2 as 60.) there is continuously fed the following mixture, in which all percentages are by weight:

ethylene glycol 83%
dimethyl terephthalate 10%
diethylene glycol 4%
triethylene glycol 1%
light impurities 2%

Also added to this feed was 100 ppm of zinc acetate as a catalyst. The column is operated with a 50% reflux ratio. The conditions at the top of the column are 150° C. and 5 psia and the conditions at the base are 209° C. and 3.5 psia. A 2% light purge was taken overhead from a condenser at the top of the column. There was recovered from the column 95% of the ethylene glycol feed as a 99% pure product. The dimethyl terephthalate feed is recovered as bishydroxyethyl terephthalate with higher glycols from the column bottom. When the zinc acetate catalyst is not present, the trays in the still and the condenser become fouled by dimethyl terephthalate.

The invention has been described by reference to preferred embodiments, but it will be understood changes can be made to the embodiments specifically described herein within the spirit and scope of the invention.

What is claimed is:

1. A process for removing dimethyl terephthalate contaminants from ethylene glycol recovered from scrap polyester by low pressure methanolysis, the process comprising a) adding an ester exchange catalyst to an otherwise catalyst-free mixture of dimethyl terephthalate and ethylene glycol and b) heating the mixture to convert dimethyl terephthalate to bishydroxyethyl terephthalate.

2. A process of claim 1, wherein heating occurs during a distillation of ethylene glycol from other components of the mixture.

3. A process of claim 2, wherein distillation is at a temperature in the range of 100° to 230° C. and a pressure in the range of 3 to 30 psia.

4. A process of claim 1 wherein the catalyst is zinc acetate.

5. A process for recovering and purifying ethylene glycol from polyester resins using a dissolver for receiving polyester, a reactor for depolymerizing polyester into monomer components, and a rectifier for separating monomer components;

the process comprising:

a) adding polyester to the dissolver and combining it with melt from the reactor to reduce the chain length of the polyester, b) transferring reduced chain length polyester from the dissolver to the reactor, c) passing super-heated methanol through the reactor to depolymerize polyester into its constituent monomers, d) transferring depolymerization products from the reactor to the rectifier, e) separating the depolymerization products in the rectifier into a vapor phase containing monomer components and a liquid phase containing higher molecular weight materials, f) recovering and purifying ethylene glycol exiting the rectifier by i) adding an ester exchange catalyst to the ethylene glycol containing mixture and ii) heating the mixture to convert dimethyl terephthalate to bishydroxyethyl terephthalate.

6. A process of claim 5, wherein heating occurs during a distillation of ethylene glycol from other components of the mixture at a temperature in the range of 100° to 230° C. and a pressure in the range of 3 to 30 psia.

7. A process of claim 6 wherein the catalyst is zinc acetate.

* * * * *

UNITED STATES PATENT AND TRADEMARK OFFICE
CERTIFICATE OF CORRECTION

PATENT NO. : 5,672,780
DATED : 30 September 1997
INVENTOR(S) : William J. Gamble, et al It is certified that error appears in the above-identified patent and that said Letters Patent is hereby corrected as shown below:

Cover page of Patent -- Related U.S. Application Data

[60] Provisional Application No. 60/002,179, Aug. 11, 1995. --

Signed and Sealed this

Twenty-ninth Day of September, 1998

Attest:

BRUCE LEHMAN

*Attesting Officer*    Commissioner of Patents and Trademarks